(12) United States Patent
Tyan

(10) Patent No.: US 12,053,354 B2
(45) Date of Patent: Aug. 6, 2024

(54) LAYERED EARPLUGS WITH PRESSURE REDUCING MECHANISM

(71) Applicant: Sasha Tyan, Gardena, CA (US)

(72) Inventor: Sasha Tyan, Gardena, CA (US)

(*) Notice: Subject to any disclaimer, the term of this patent is extended or adjusted under 35 U.S.C. 154(b) by 80 days.

(21) Appl. No.: 17/399,715

(22) Filed: Aug. 11, 2021

(65) Prior Publication Data
US 2023/0048416 A1 Feb. 16, 2023

(51) Int. Cl.
*A61F 11/08* (2006.01)

(52) U.S. Cl.
CPC .............. *A61F 11/08* (2013.01); *A61F 11/085* (2022.01); *A61F 2210/0076* (2013.01); *A61F 2230/0021* (2013.01)

(58) Field of Classification Search
CPC ........ A61F 11/08; A61F 11/085; A61F 11/06; A61F 2210/0076; A61F 2230/0021; H04R 1/1016; H04R 25/652; H04R 25/656; H04R 2460/09; H04R 2460/11
See application file for complete search history.

(56) References Cited

U.S. PATENT DOCUMENTS

| | | | | |
|---|---|---|---|---|
| 2,437,490 A * | 3/1948 | Watson | ............ | A61F 11/08 128/867 |
| 3,080,011 A * | 3/1963 | Henderson | ............ | H04R 25/656 128/868 |
| 4,143,657 A * | 3/1979 | Takeda | ............ | A61F 11/085 128/867 |
| 5,024,612 A * | 6/1991 | van den Honert | ...... | A61F 11/10 604/36 |
| 5,153,387 A * | 10/1992 | Zwislocki | ............ | H04R 25/658 181/129 |
| 5,819,745 A * | 10/1998 | Mobley | ............ | A61F 11/08 128/867 |
| 6,129,086 A * | 10/2000 | Gzybowski | ............ | A61F 11/00 482/13 |
| 6,820,717 B2 * | 11/2004 | Fleming | ............ | A61F 11/10 181/134 |
| 8,054,985 B2 * | 11/2011 | Doty | ............ | A61F 11/12 381/328 |
| 11,266,532 B2 * | 3/2022 | Van 'T Hof | ............ | H04R 25/652 |
| 2002/0066455 A1 | 6/2002 | Falco | | |
| 2003/0159878 A1 * | 8/2003 | Hakansson | ............ | A61F 11/08 181/135 |

(Continued)

FOREIGN PATENT DOCUMENTS

| | | | | |
|---|---|---|---|---|
| CN | 110351625 B | * | 10/2020 | |
| KR | 20160027003 A | * | 3/2016 | |
| KR | 200483115 Y1 | * | 4/2017 | |

*Primary Examiner* — Edgardo San Martin
(74) *Attorney, Agent, or Firm* — UCLA Patent Law Clinic

(57) ABSTRACT

A layered earplug with pressure reducing mechanisms in accordance with embodiments of the invention are disclosed. In one embodiment, the layered earplug comprises: a stalk comprising a tunnel that transverses the layered earplug; a plurality of discs attached to the stalk, wherein each disc of the plurality of discs includes a diameter relative to on a position of the disc on the stalk; at least one pocket located between two adjacent discs of the plurality of discs, wherein the at least one air pocket and the plurality of discs reduce sound that reaches a user's eardrum; and at least one valve located within the tunnel configured to release accumulated air pressure in a user's ear canal through the tunnel.

18 Claims, 8 Drawing Sheets

(56) References Cited

U.S. PATENT DOCUMENTS

2004/0069310 A1  4/2004  Falco
2004/0163653 A1* 8/2004  Fleming .................. A61F 11/08
                                                   128/864

* cited by examiner

LAYERED EARPLUGS WITH PRESSURE REDUCING MECHANISM

FIELD OF THE INVENTION

The present invention generally relates to earplugs, and more specifically to layered earplugs with pressure reducing mechanisms.

BACKGROUND

Earplugs are devices that are inserted into a user's ear canals. For example, earplugs may be used to reduce the effects of loud noises. In such uses, earplugs may reduce the sound volume and thus prevent negative effects on the user such as, but not limited to, hearing loss and tinnitus. In addition, earplugs may also be utilized to prevent intrusion into the ear canal. For example, earplugs may keep out water, dust, wind, etc. Further, earplugs may also protect ears from the pain caused by pressure changes such as pressure changes in an airplane cabin.

SUMMARY OF THE INVENTION

The various embodiments of the present layered earplugs contain several features, no single one of which is solely responsible for their desirable attributes. Without limiting the scope of the present embodiments, their more prominent features will now be discussed below. In particular, the present layered earplugs will be discussed in the context of layered earplugs with pressure reducing mechanisms. However, the use of particular layered earplugs are merely exemplary and various other layered earplugs may be utilized for pressure reducing mechanisms as appropriate to the requirements of a specific application in accordance with various embodiments of the invention. After considering this discussion, and particularly after reading the section entitled "Detailed Description," one will understand how the features of the present embodiments provide the advantages described here.

In a first aspect, a layered earplug is provided, the layered earplug comprising an outer portion comprising: a stalk comprising a tunnel that transverses the layered earplug; a plurality of discs attached to the stalk, wherein each disc of the plurality of discs includes a diameter relative to on a position of the disc on the stalk; at least one pocket located between two adjacent discs of the plurality of discs, wherein the at least one air pocket and the plurality of discs reduce sound that reaches a user's eardrum; and at least one valve located within the tunnel configured to release accumulated air pressure in a user's ear canal through the tunnel.

In an embodiment of the first aspect, the tunnel has at least two walls that are opposite and parallel.

In another embodiment of the first aspect, the stalk includes a tip and an end, and wherein the plurality of discs increases in diameter based on a position moving away from the tip towards the end.

In another embodiment of the first aspect, the at least one valve is oriented at an angle less than 90 degrees toward the tip and away from the end.

In another embodiment of the first aspect, the at least one valve includes a first end and a second end, wherein the first end is attached to the stalk.

In another embodiment of the first aspect, the first end of the at least one valve is closer to the tip than the second end of the at least one valve.

In another embodiment of the first aspect, the second end of the at least one valve is detached from the stalk allowing the at least one valve to open releasing accumulated air pressure through the tunnel.

In another embodiment of the first aspect, the plurality of discs is layered with equal space in between each disc of the plurality of discs.

In another embodiment of the first aspect, the at least one valve is in an open configuration to allow air pressure to escape from within the user's ear canal.

In another embodiment of the first aspect, the at least one valve is in a closed configuration when air pressure in the user's ear canal has not accumulated above a release pressure.

In another embodiment of the first aspect, wherein each of the plurality of discs has a thickness of 0.5 mm.

In another embodiment of the first aspect, wherein each of the plurality of air pockets has a thickness of 0.5 mm.

In another embodiment of the first aspect, the at least one valve is oriented at an angle of 30 degrees.

In another embodiment of the first aspect, the at least one valve has a thickness of 0.5 mm.

In another embodiment of the first aspect, the stalk has a thickness of 5 mm.

In another embodiment of the first aspect, the stalk has a length of 30 mm.

In another embodiment of the first aspect, the tunnel is square shaped.

In another embodiment of the first aspect, the stalk includes a tip and an end, and the tunnel is narrower at the tip than at the end of the stalk.

In another embodiment of the first aspect, the square shape has sides that are 1 mm at the tip and 2 mm at the end of the stalk.

In another embodiment of the first aspect, the layered earplug further comprises a handle.

BRIEF DESCRIPTION OF THE DRAWINGS

The various embodiments of the present layered earplugs with pressure reducing mechanisms now will be discussed in detail with an emphasis on highlighting the advantageous features. These embodiments depict the novel and non-obvious layered earplugs with pressure reducing mechanisms shown in the accompanying drawings, which are for illustrative purposes only. These drawings include the following figures.

DETAILED DESCRIPTION OF THE DRAWINGS

Figure 1:
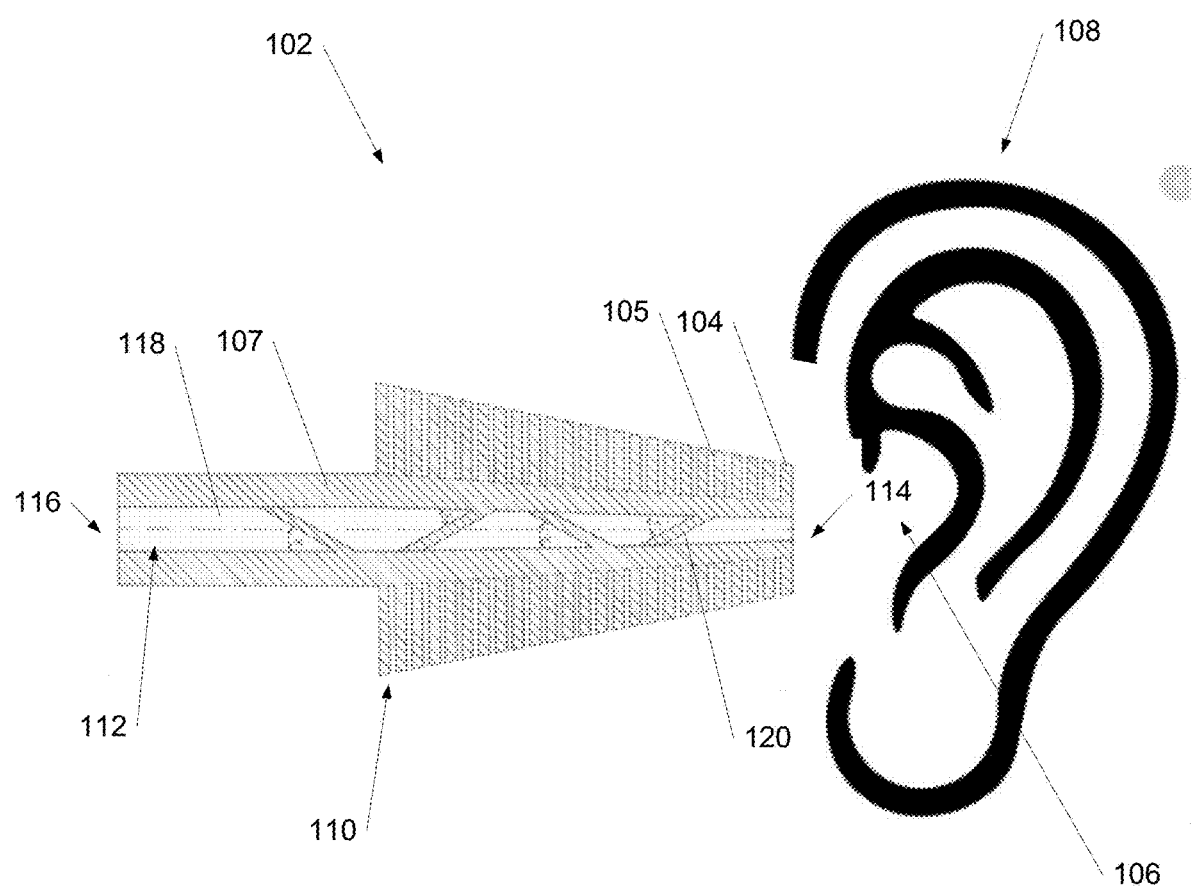
FIG. 1 illustrates a layered earplug with a pressure reducing mechanism in accordance with an embodiment of the invention.

The following detailed description describes the present embodiments with reference to the drawings. In the drawings, reference numbers label elements of the present embodiments. These reference numbers are reproduced below in connection with the discussion of the corresponding drawing features.

Turning now to the drawings, layered earplugs with pressure reducing mechanisms in accordance with embodiments of the invention are illustrated. In many embodiments, layered earplugs may be configured to minimize the amount of sound from the outside environment reaching a user's ear drum and/or for reducing the air pressure inside of the ear canal, as further described below. In many embodiments, layered earplugs may include an outer portion that may be in contact with a user's ear canal and an inner portion, as further described below. In some embodiments, the outer portion may include one or more discs configured to fit varying sizes of ear canals. For example, in some embodiments, the disc(s) may increase in diameter based on the position of the disc(s) relative to a tip portion of the layered earplug (may also be referred to as a "tip portion of the stalk"). In various embodiments, the layered earplugs may also include air pockets created by the spacing between discs, as further described below. In several embodiments, the air pockets may minimize the amount of sound that passes through a user's ear canal.

In many embodiments, the layered earplugs may also include an inner portion that may include a stalk member having a tunnel, as further described below. In some embodiments, the tunnel may transverse through a center of the layered earplug. In some embodiments, the tunnel may include one or more valves regulated by air pressure. For example, when air pressure has not accumulated in the ear canal, the valve(s) may close, thereby minimizing the amount of sound passing through a user's ear canal. In contrast, when air pressure has accumulated in the ear canal, the valves may open to reduce the accumulated air pressure. In a variety of embodiments, the valve(s) be attached on one end (e.g., a first end of the valve) to one side of the stalk member, and on the other end (e.g., a second end of the valve), may be unattached to the other side of the stalk member, as further described below. In many embodiments, as air pressure accumulates in the ear canal, the unattached end of the valve (e.g., the second end of the valve) may open (may also be referred to as an "open configuration") to allow accumulated air pressure to escape. When the air pressure is reduced, the unattached end of the valve (e.g., the second end of the valve) may remain closed (may also be referred to as a "closed configuration"), resting unattached to the inner portion.

In some embodiments, the stalk member may create a tunnel that has opposite and parallel walls. For example, in some embodiments, the stalk member may create a tunnel that is square or rectangular. In some embodiments, the first end of a valve may attach to one wall of the tunnel and second end of the valve may be unattached to the opposite wall of the tunnel. In some embodiments, the stalk member may create a tunnel that may be uniform from the tip to an end of the layered earplug. In some embodiments, the stalk member may create a tunnel that varies in dimension from the tip to the end of the layered earplug. For example, the tunnel may be narrower at the tip and widen as the tunnel transverses the length of the layered earplug towards the end. Layered earplugs in accordance with embodiments of the invention are further discussed below.

Layered Earplugs

Typically, traditional earplugs may cause users discomfort, because the earplug does not fit properly in the user's ear canal. In addition, traditional earplugs may cause discomfort due to air pressure building up inside of the ear canal when the earplugs are inserted. A layered earplug with a pressure reducing mechanism in accordance with an embodiment of the invention is shown in FIG. 1. In many embodiments, the layered earplug 102 may be inserted into an ear canal 106 of a user's ear 108. In various embodiments, the layered earplug 102 may include an outer portion 110 and an inner portion 112. When the layered earplug 102 is inserted into the user's ear canal 106, the outer portion 110 may abut against the ear canal 106 thereby reducing the amount of sound that may travel the user's ear canal 106 and ultimately reaching the user's eardrum, as further described below. In addition, the outer portion 110 may help the layered earplug 102 fit varying sizes of ear canals 106, as further described below. In several embodiments, the inner portion 112 may help to reduce air pressure in the user's ear canal 106 by allowing air to escape when air pressure builds up in the ear canal 106, as further described below.

In reference to FIG. 1, the layered earplug may include one or more discs 104 which may be connected to a stalk member 107 (may also be referred to as "stalk") that transverses the length of the layered earplug 102. In some embodiments, the discs 104 may increase in diameter from a tip portion 114 to an end portion 116 of the stalk. In some embodiments, the increase in diameter of the discs 104 may allow the earplug 102 to fit into varying sizes of ear canals 106. In some embodiments, the change in diameter of the discs 104 would result in the user being able to insert the layered earplug 102 to a depth depending on the size and shape of the particular ear canal. For example, for a narrow ear canal 106, the layered earplug 102 may insert less than for a wider ear canal 106 as the discs 104 have a smaller diameter towards the tip portion 114 than at the end portion 116. Likewise, for a wide ear canal 106, the layered earplug 102 may insert further than for a narrower ear canal 106. In some embodiments, the material selection (e.g., a flexible material) of the layered earplug 102 may also assist in fitting a shape of a user's ear canal 106.

In further reference to FIG. 1, the layered earplug 102 may include one or more air pockets 105, as further described below. For example, an air pocket 105 may be located in between two discs. In some embodiments, the discs (e.g., disc 104) and the air pocket (e.g., air pocket 105) may reduce the amount of sound that reaches the user's eardrum, as further described below. For example, the discs and the air pockets may reduce the amount of sound by reflecting sound waves. In some embodiments, the repetitive discs and air pockets may act as consecutive barriers that trap soundwaves thereby reducing noise.

In further reference to FIG. 1, the stalk member 107 may include a tunnel 118 that may transverse through a center of the layered earplug 102. In many embodiments, the tunnel 118 may include one or more valves 120 positioned within the tunnel 118, as further described below. In some embodiments, a first end of the valve 120 may be attached on one side of the tunnel 118 and a second end of the valve 120 may be unattached on the other side of the tunnel 118, as further described below. In some embodiments, the valve 120 may be attached to the tunnel at an angle, as further described below. In some embodiments, the unattached side of the valve 120 may allow air to escape when air pressure builds up in the ear canal 106, thereby improving the user's comfort. For example, the valve 120 may slightly open to channel away the air that is trapped in the ear canal 106. In some embodiments, the valve 120 may close and act as a barrier, to reduce the sound waves that reach the user's ear drum. Although specific layered earplugs are discussed above with respect to FIG. 1, any of a variety of earplugs including a variety of sound reducing and pressure reducing mechanisms as appropriate to the requirements of a specific application can be utilized in accordance with embodiments of the invention.

Layered Earplugs with Uniform Tunnels

Layered earplugs may include a stalk having a hollow cavity (may be referred to as a "tunnel") that may have uniform dimensions. In particular, the shape of the tunnel may be uniform along the length of the stalk. For example, the tunnel may have a three-dimensional ("3D") shape having a two-dimensional ("2D") face and a length. In some embodiments, the 2D face may be a square having sides that are uniform (i.e., unchanging in dimension) along the length of the stalk. In some embodiments, the 2D face may be a circle having a radius that is uniform along the length of the stalk. In earplugs with uniform tunnels, the 2D face may take on any shape that may be uniform along the length of the stalk.

Figure 2:
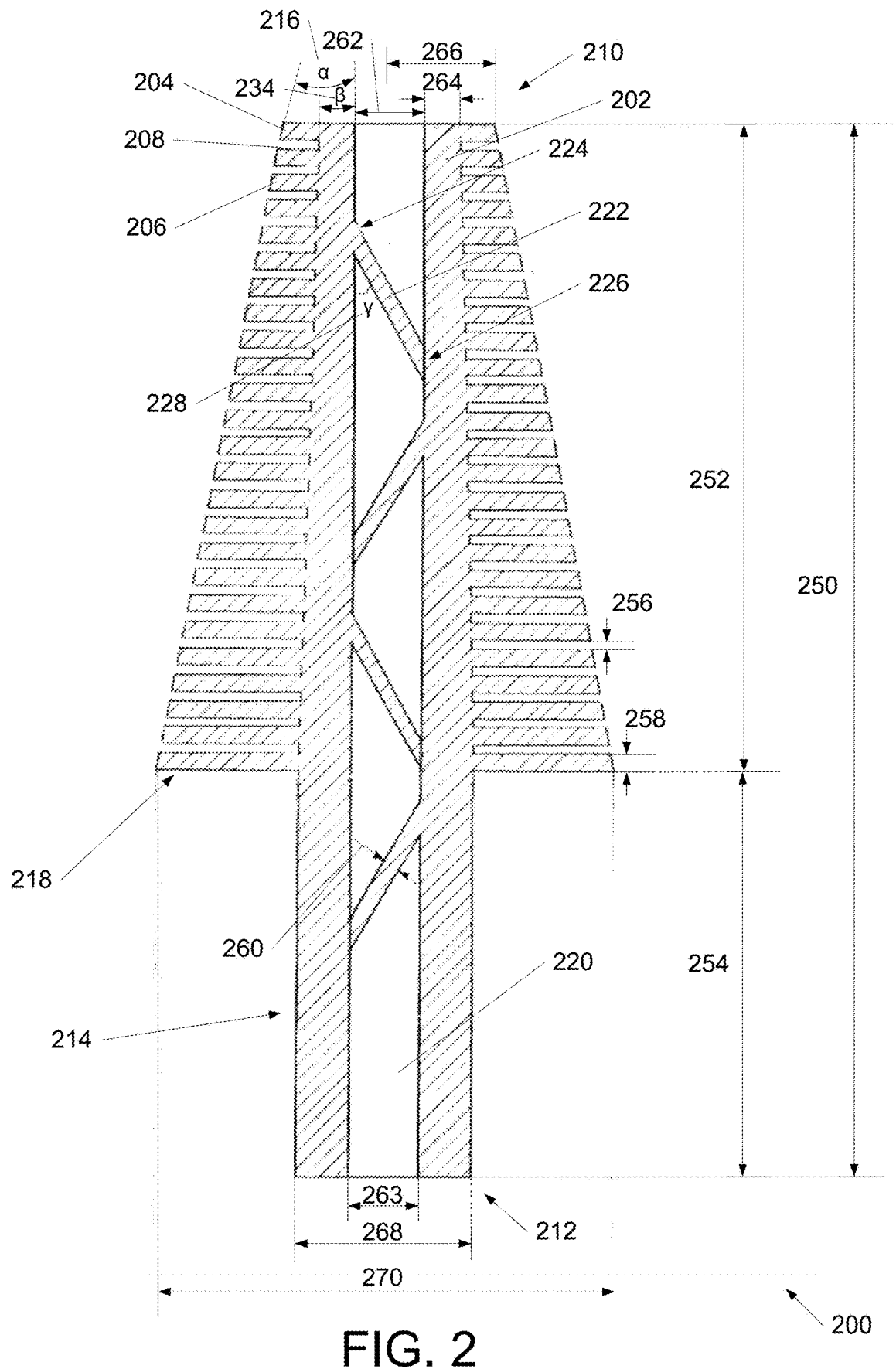
FIG. 2 is a side view of a layered earplug with a uniform tunnel in accordance with an embodiment of the invention.

A side view of a layered earplug with a uniform tunnel in accordance with an embodiment of the invention is shown in FIG. 2. The layered earplug 200 may include one or more discs 204, 206 connected to a stalk 202 that may transverse a length of the layered earplug 200. In many embodiments, the layered earplug 200 may include a tip portion 210 (may also be referred to as a "tip") indicating the side of the earplug 200 that inserts into a user's ear. In addition, the layered earplug 200 may also include an end portion 212 (may also be referred to as an "end") indicating the side of the earplug 200 that remains outside of the user's ear when in use. In some embodiments, the layered ear 200 may also have a handle 214 that allows the user to hold the layered earplug 200 when inserting and/or removing the layered earplug 200 from the user's ear.

In reference to FIG. 2, the discs 204, 206 may increase in diameter from the tip 210 to the trailing edge 218 and/or the end 212. For example, the discs may increase in diameter based on an angle α 216 relative to the stalk 202. In many embodiments, the increase in diameter of the discs may allow the earplug 200 to fit into varying sizes of ear canals, as further described above. In many embodiments, the discs may have a smaller diameter towards the tip 210 than at the end 212. In some embodiments, the layered earplug 200 may include a trailing edge 218 created by a disc that is furthest away from the tip 210. In addition, an air pocket 208 may be located in between any two discs (e.g., between disc 204 and disc 206). In some embodiments, the discs (e.g., disc 204 and 206) and the air pocket (e.g., air pocket 208) may reduce the amount of sound that reaches the user's eardrum, as described herein.

In further reference to FIG. 2, the stalk 202 may include a tunnel 220 that may transverse the length of the stalk 202. In many embodiments, the tunnel 220 may include one or more valves 222 positioned within the tunnel 220. In some embodiments, a first end 224 of the valve 222 may be attached on one side of the tunnel 220 and a second end 226 of the valve 222 may be unattached on the other side of the tunnel 220. In some embodiments, the valve 222 may be attached to the tunnel at an angle γ 228. In many embodiments, the second end 226 the valve 222 may open and close to allow air to escape when air pressure builds up in the ear canal utilizing valve mechanics known to one of ordinary skill in the art.

In further reference to FIG. 2, the layered earplug 200 may have predetermined measurements in maintaining a uniform tunnel 220. Below are some exemplary measurements for illustrative purposes only. In some embodiments, a stalk length 250 may be 30 mm, from tip 210 to trailing edge 218 length 252 may be 18.5 mm, and handle length 254 may be 11.5 mm. In some embodiments, an air pocket thickness 256 may be 0.5 mm, a disc thickness 258 may be 0.5 mm, and a valve thickness 260 may be 0.5 mm. At the tip 210, the tunnel width 262 (and/or height and/or diameter) may be 2 mm and the stalk diameter may be 4 mm. At the tip 210, a stock thickness 266 may be 1 mm and a distance 266 from a center of the tunnel 220 and an edge of the first disc 204 may be 3 mm. At the end 212, the tunnel width 263 (and/or height and/or diameter) may be 2 mm and the stalk diameter 268 may be 5 mm. In some embodiments, the trailing edge diameter 270 may be 13 mm. In some embodiments, the stalk diameter 268 may remain uniform or vary from the tip 210 to the end 212. In some embodiments, the stalk thickness 264 (and the stalk diameter 268) may change based on a 13 angle 234. In some embodiments, the β angle 234 may be 2 degrees relative to an axis running through the center of the tunnel 220.

Figure 3:
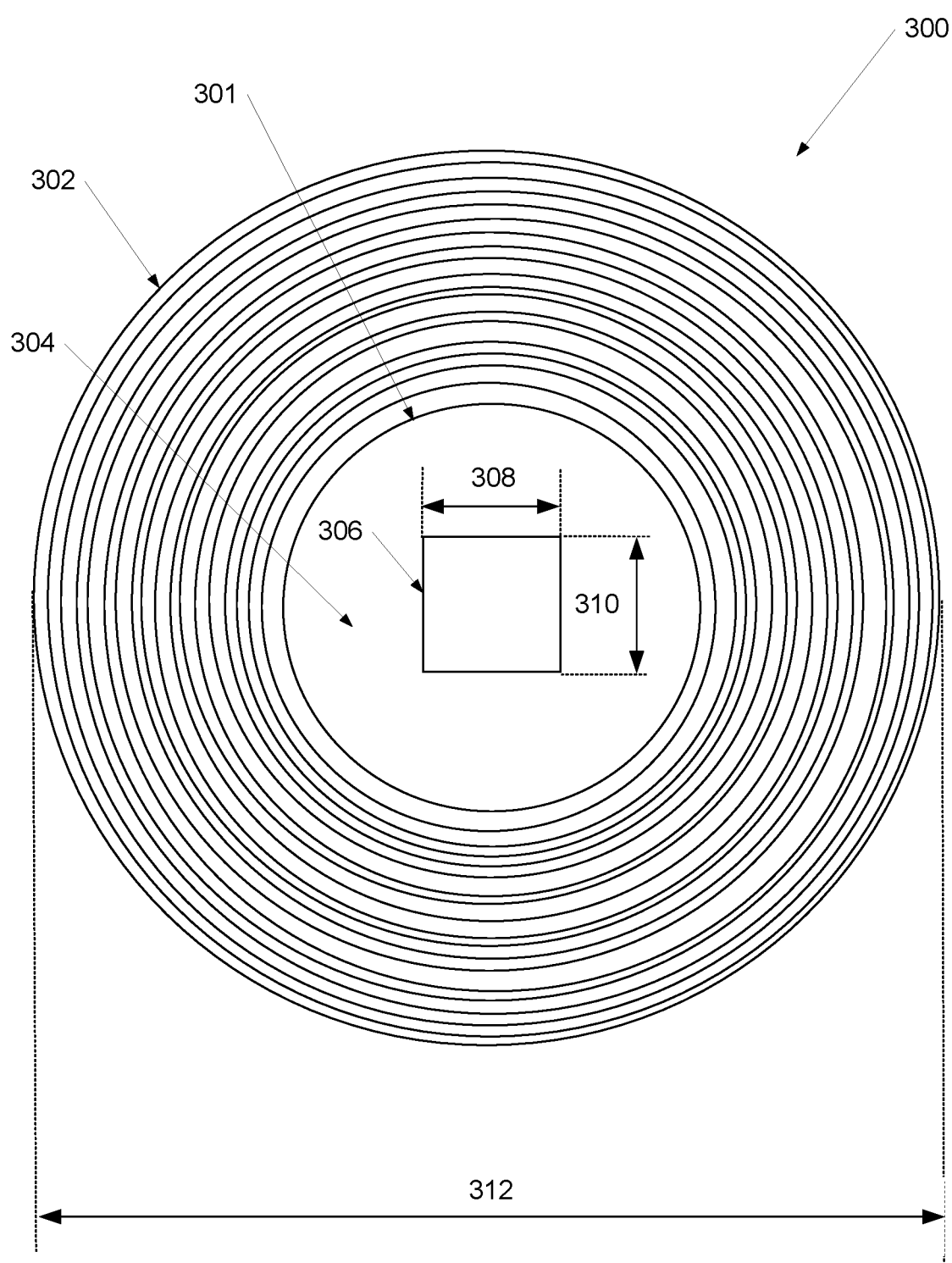
FIG. 3 is a top view of a layered earplug with a uniform tunnel in accordance with an embodiment of the invention.

A top view of a layered earplug with a uniform tunnel in accordance with an embodiment of the invention is shown in FIG. 3. The layered earplug 300 may include including a plurality of discs, as further described above. For example, the layered earplug 300 may include a disc 301 that is located near or at a tip of the stalk 304 and a disc 302 that is located near or at the trailing edge, as further described above. In some embodiments, the change in diameter of the plurality of discs (e.g., discs 301, 302) may allow the user to insert the layered earplug 300 to a depth depending on the size and shape of the user's ear canal. In some embodiments, the disc 301 located closer to the tip may have a smaller than a diameter of the disc located closer to the trailing edge. For any number of discs 301, 302, the diameter 312 (e.g., 13 mm) of the disc 302 at the trailing edge may be the maximum diameter of the layered earplug 300. In many embodiments, the layered earplug 300 may include a tunnel having a 2D face 306, measured at the tip, having a width 308 and a height 310. In some embodiments, the 2D face 306 may be a square with the width 308 being equal to the height 310 (e.g., 2 mm and 2 mm, respectively).

Figure 4:
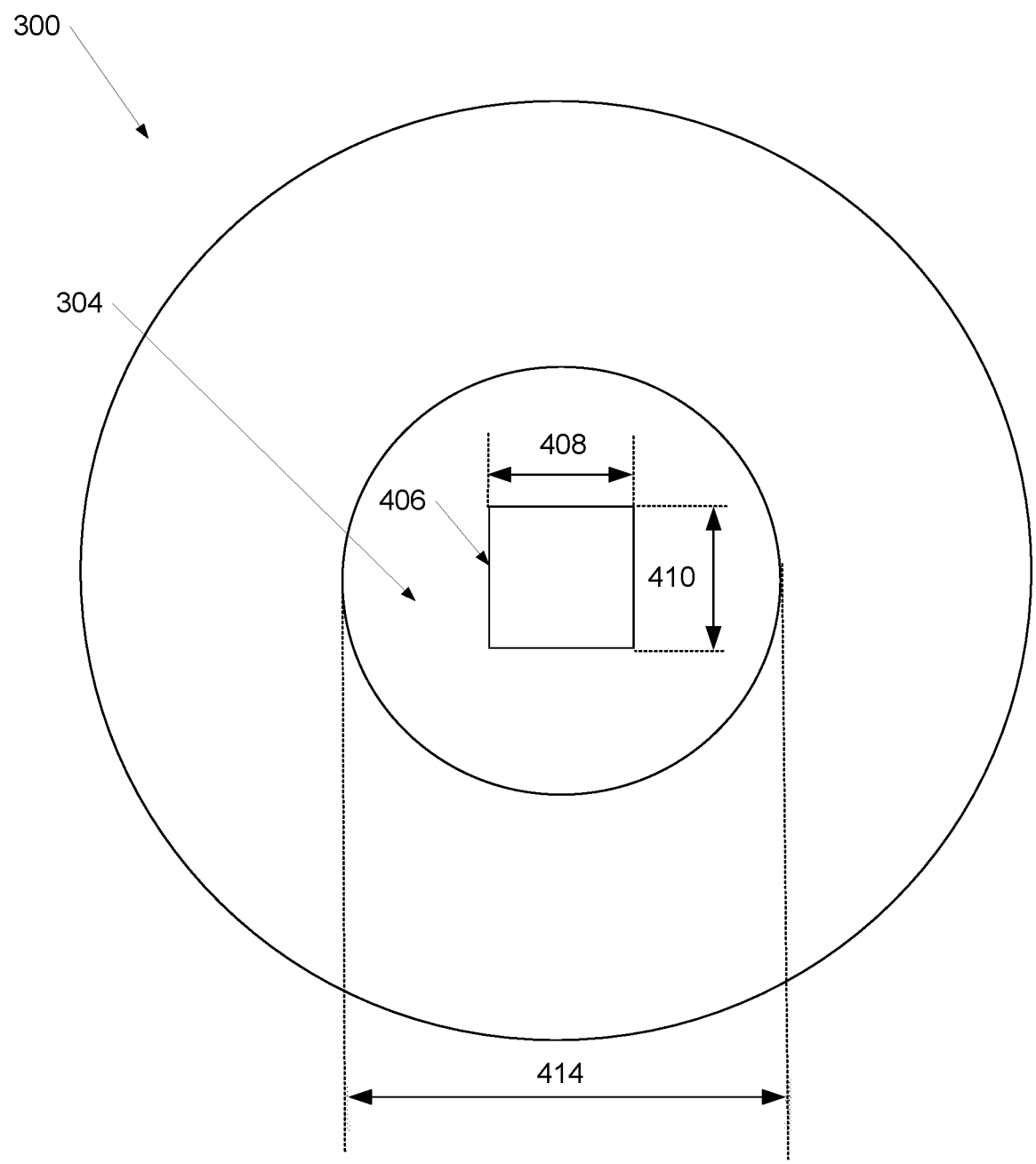
FIG. 4 is a bottom view of a layered earplug with a uniform tunnel in accordance with an embodiment of the invention.

A bottom view of a layered earplug with a uniform tunnel in accordance with an embodiment of the invention is shown in FIG. 4. With a uniform tunnel, the stalk 304 of the layered earplug 300 may include a 2D face 406 having a width 408 and a height 410 that is equal when measured at the tip and the end of the layered earplug 300. For example, the 2D face 406 measured at the end of the layered earplug 300 (as illustrated in FIG. 4) may be equal to the 2D face 306 measured at the tip of the layered earplug 300 (as illustrated in FIG. 3). In some embodiments, the 2D face 406 may be a square with the width 408 being equal to the height 410 (e.g., 2 mm and 2 mm, respectively). The stalk may take on various shapes and sized. For example, the stalk 304 may be a cylinder having a diameter 414 (e.g., 5 mm).

Although specific layered earplugs with uniform tunnels are discussed above with respect to FIGS. 1-4, any of a variety of earplugs including a variety of uniform tunnel shapes, sound reducing and pressure reducing mechanisms as appropriate to the requirements of a specific application can be utilized in accordance with embodiments of the invention. Layered earplugs with varying tunnel shapes in accordance with embodiments of the invention are discussed further below.

Layered Earplugs with Varying Tunnels

Layered earplugs may include stalks that may have varying sizes and shapes. In particular, the shape of the tunnel may vary along the length of the stalk. For example, the tunnel may have a three-dimensional ("3D") shape having a 2D face that varies (i.e., changes) in size and/or shape along the length of the tunnel. In some embodiments, the 2D face may be a square having sides that vary (i.e., changing in dimension) along the length of the stalk. In some embodiments, the 2D face may vary along the stalk from a tip to the trailing end of the stalk. In some embodiments, the 2D face may vary along the entire length of the stalk (e.g., from tip to end). In some embodiments, the 2D face may be a circle having a radius that varies along the length of the stalk. In layered earplugs with varying tunnels, the 2D face may take on any shape that may be vary along any portion of the length of the stalk.

Figure 5:
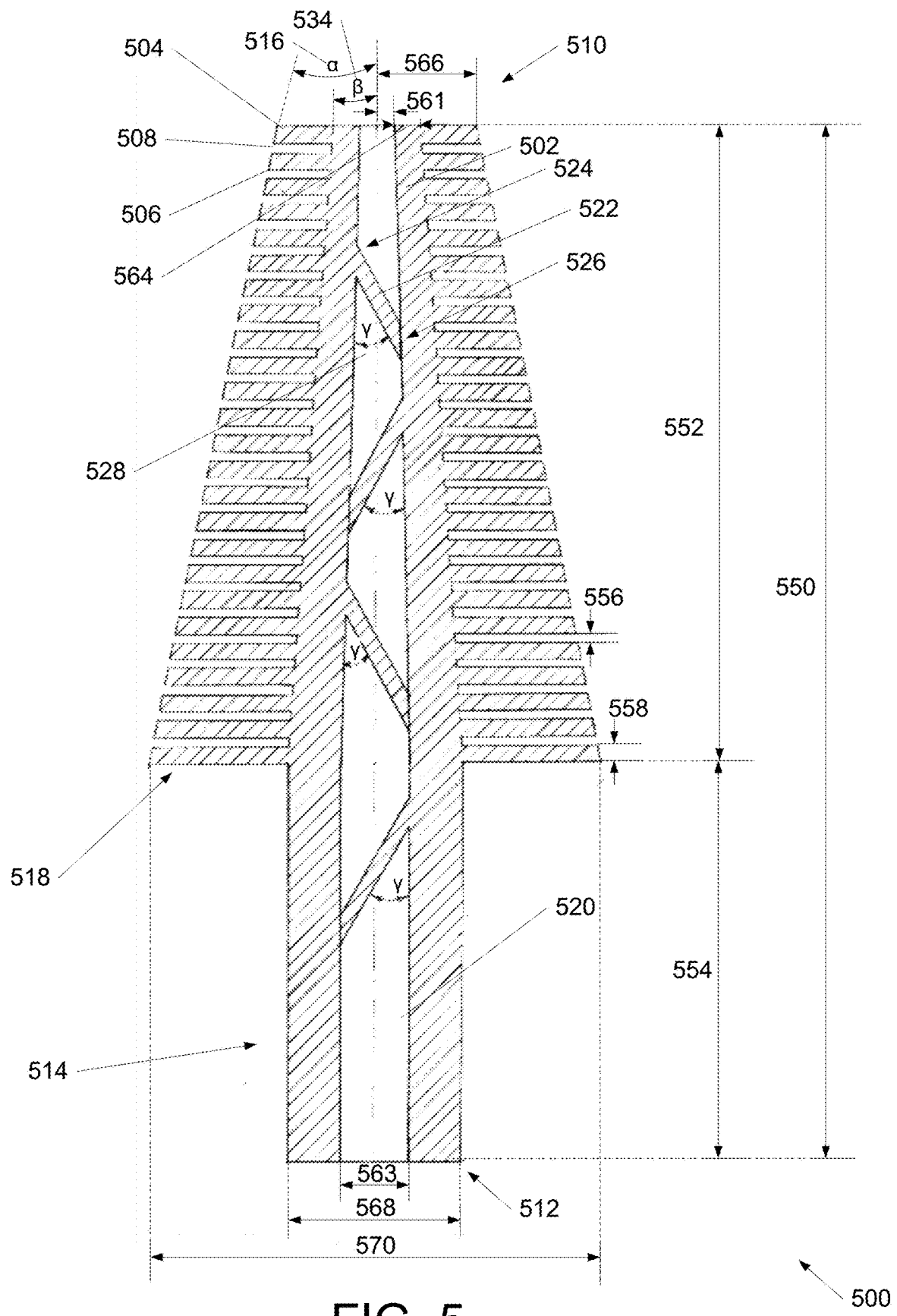
FIG. 5 is a side view of a layered earplug with a varying tunnel in accordance with an embodiment of the invention.

A side view of a layered earplug with a varying tunnel in accordance with an embodiment of the invention is shown in FIG. 5. The layered earplug 500 may include one or more discs 504, 506 connected to a stalk 502 that may transverse a length of the layered earplug 500. In many embodiments, the layered earplug 500 may include a tip 510 indicating the side of the earplug 500 that inserts into a user's ear. In addition, the layered earplug 500 may also include an end 512 indicating the side of the earplug 500 that remains outside of the user's ear when in use. In some embodiments, the layered ear 500 may also have a handle 514, as further described above.

In reference to FIG. 5, the discs 504, 506 may increase in diameter from the tip 510 to the trailing edge 518 and/or the end 512, as further described above. For example, the discs may increase in diameter based on an angle α 516 relative to the stalk 502. In some embodiments, the layered earplug 500 may include a trailing edge 518 created by a disc that is furthest away from the tip 510. In addition, an air pocket 508 may be located in between any two discs (e.g., between disc 504 and disc 506), as further described above. In some embodiments, the angle α 516 may be 12 degrees relative to an axis running through the center of the tunnel 520.

In further reference to FIG. 5, the stalk 502 may include a tunnel 520 that may transverse the length of the stalk 502. In many embodiments, the tunnel 520 may include one or more valves 522, as further described above. In some embodiments, a first end 524 of the valve 522 may be attached on one side of the tunnel 520 and a second end 526 of the valve 522 may be unattached on the other side of the tunnel 520, as further described above. In some embodiments, the valve 522 may be attached to the tunnel at an angle γ 528, as further described above. In some embodiments, the angle γ 528 may be 30 degrees relative to an axis running through the center of the tunnel 520.

In further reference to FIG. 5, the layered earplug 500 may have predetermined measurements in maintaining a varying tunnel 520. Below are some exemplary measurements for illustrative purposes only. In some embodiments, a stalk length 550 may be 30 mm, from tip 510 to trailing edge 518 length 552 may be 18.5 mm, and handle length 554 may be 11.5 mm. In some embodiments, an air pocket thickness 556 may be 0.5 mm and a disc thickness 558 may be 0.5 mm. At the tip 510, the tunnel width (and/or height and/or diameter) may be 1 mm (i.e., 2 times the tunnel half width 561 of 0.5 mm). At the tip 210, a distance 566 from a center of the tunnel 520 and an edge of the first disc 504 may be 3 mm. At the end 512, the tunnel width 563 (and/or height and/or diameter) may be 2 mm and the stalk diameter 568 may be 5 mm. In some embodiments, the trailing edge diameter 570 may be 13 mm. In some embodiments, the stalk diameter 568 may vary from the tip 510 to the end 512. In some embodiments, the stalk thickness 564 may change based on a β angle 534. In some embodiments, the β angle 534 may be 4 degrees relative to an axis running through the center of the tunnel 520. In some embodiments, the stalk thickness 564 (and the tunnel diameter 563) may vary from the tip 510 to the trailing edge 518 and be uniform from trailing edge 518 to end 512. In some embodiments, the stalk thickness 564 (and the tunnel diameter 563) may vary from the tip 510 to the end 512.

Figure 6:
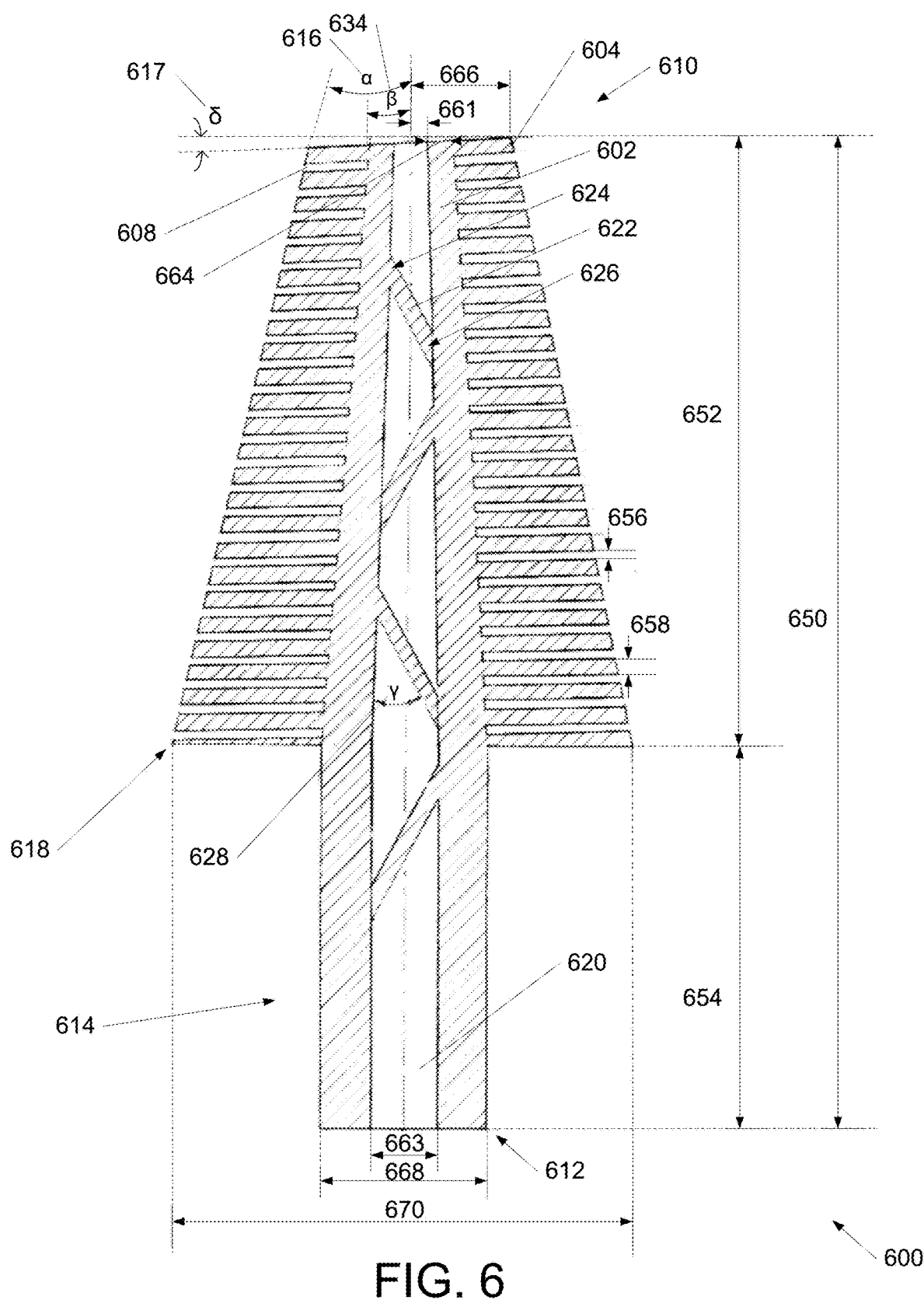
FIG. 6 is a side view of a layered earplug with a varying tunnel utilizing a spiral member in accordance with an embodiment of the invention.

In some embodiments, the plurality of discs may take on various configuration. For example, in some embodiments, a single spiral member may be utilized for the functions of the plurality of discs. A side view of another layered earplug with a varying tunnel utilizing a spiral member in accordance with an embodiment of the invention is shown in FIG. 6. The layered earplug 600 may include a spiral member 604 that wraps around a stalk 602. In many embodiments, the spiral member 604 may wrap around the diameter of the stalk 602 from the tip 610 to the trailing edge 618. In some embodiments, the spiral member 604 may stop wrapping to provide for a handle 614, as further described above. In some embodiments, the spiral member 604 may wrap around the diameter of the stalk 602 from the tip 610 to an end 612. In some embodiments, the spiral member 604 may create a gap based on an angle δ 617. In some embodiments, the angle δ 617 may be 3 degrees relative to a horizontal axis that is perpendicular to an axis running through the center of the tunnel 620.

In reference to FIG. 6, the spiral member 602 may increase in diameter from the tip 510 to the trailing edge 618 (and/or the end 612), as further described above. For example, the spiral member 604 may increase in diameter based on an angle α 616 relative to the stalk 602. In addition, an air pocket 608 may be located in between any gap of the spiral member 604 as it wraps around the diameter of the stalk 602. In some embodiments, the angle α 616 may be 12 degrees relative to an axis running through the center of the tunnel 620.

In further reference to FIG. 6, the stalk 602 may include a tunnel 620 that may transverse the length of the stalk 602. In many embodiments, the tunnel 620 may include one or more valves 622, as further described above. In some embodiments, a first end 624 of the valve 622 may be attached on one side of the tunnel 620 and a second end 626 of the valve 622 may be unattached on the other side of the tunnel 620, as further described above. In some embodiments, the valve 622 may be attached to the tunnel at an angle γ 628, as further described above. In some embodiments, the angle γ 628 may be 30 degrees relative to an axis running through the center of the tunnel 620.

In further reference to FIG. 6, the layered earplug 600 may have predetermined measurements in maintaining a varying tunnel 620. Below are some exemplary measurements for illustrative purposes only. In some embodiments, a stalk length 650 may be 30 mm, from tip 610 to trailing edge 618 length 552 may be 18.5 mm, and handle length 654 may be 11.5 mm. In some embodiments, an air pocket thickness 656 may be 0.5 mm and a spiral member thickness 658 may be 0.5 mm. At the tip 610, the tunnel width (and/or height and/or diameter) may be 1 mm (i.e., 2 times the tunnel half width 661 of 0.5 mm). At the tip 610, a distance 666 from a center of the tunnel 620 and an edge of the spiral member 604 may be 3 mm. At the end 612, the tunnel width 663 (and/or height and/or diameter) may be 2 mm and the stalk diameter 668 may be 5 mm. In some embodiments, the trailing edge diameter 670 may be 13 mm. In some embodiments, the stalk diameter 668 may vary from the tip 510 to the end 512. In some embodiments, the stalk thickness 664 may change based on a β angle 634. In some embodiments, the β angle 634 may be 4 degrees relative to an axis running through the center of the tunnel 620. In some embodiments, the stalk thickness 664 (and the tunnel diameter 663) may vary from the tip 610 to the trailing edge 618 and be uniform from trailing edge 618 to end 612. In some embodiments, the stalk thickness 664 (and the tunnel diameter 663) may vary from the tip 610 to the end 612.

Figure 7:
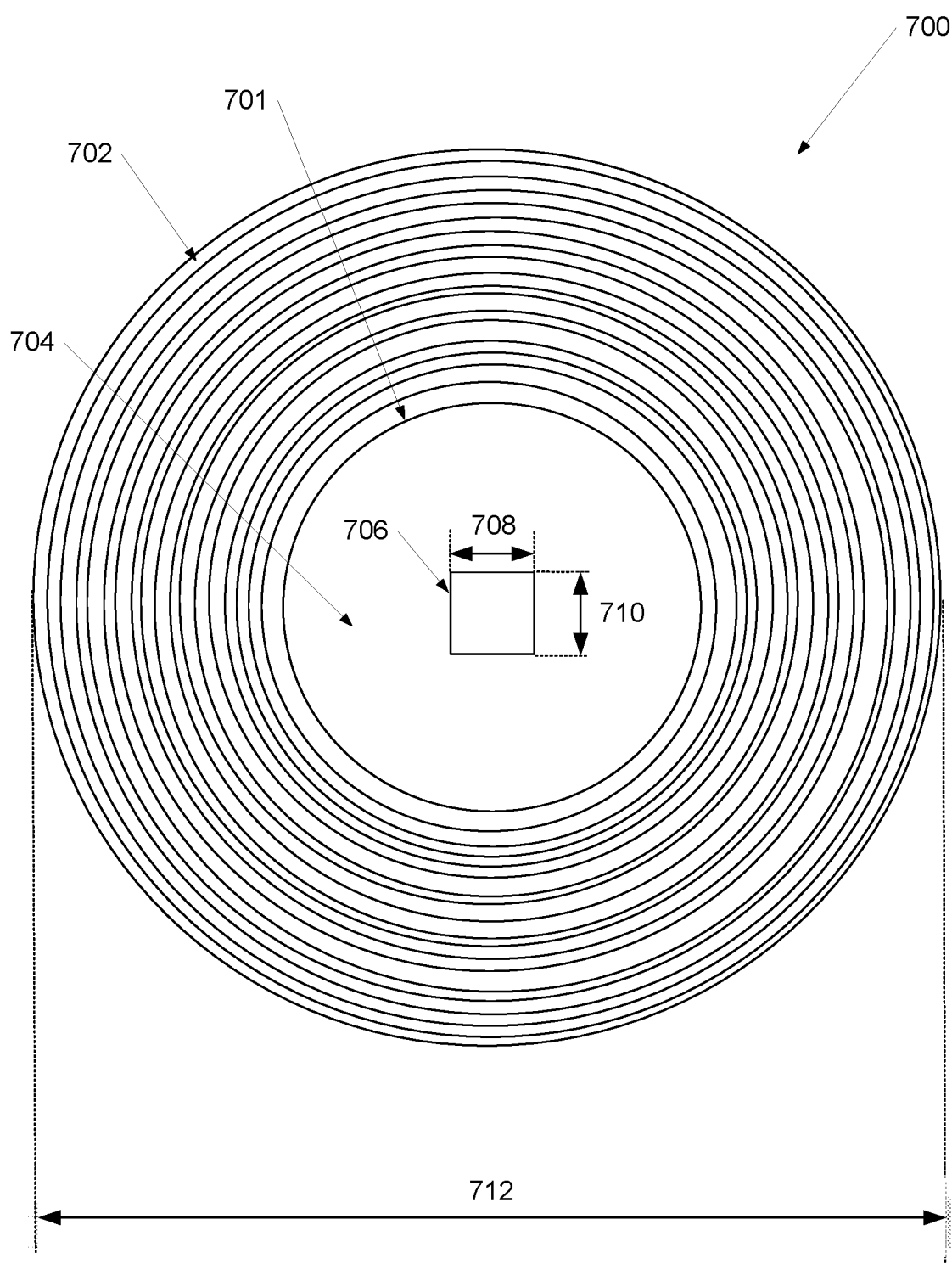
FIG. 7 is a top view of a layered earplug with a varying tunnel in accordance with an embodiment of the invention.

A top view of a layered earplug with a varying tunnel in accordance with an embodiment of the invention is shown in FIG. 7. For example, the varying tunnel may be a tunnel for layered earplug 500 and/or layered earplug 600, as further described above. In reference to FIG. 7, the layered earplug 700 may include including a plurality of discs or a spiral member, as further described above. For example, the layered earplug 700 may include a disc 701 (or portion of the spiral member) that is located near or at a tip of the stalk 704 and a disc 702 (or portion of the spiral member) that is located near or at the trailing edge, as further described above. In some embodiments, the change in diameter of the plurality of discs (e.g., discs 701, 702) (or the spiral member) may allow the user to insert the layered earplug 700 to a depth depending on the size and shape of the user's ear canal. In some embodiments, the disc 701 (or portion of the spiral member) located closer to the tip may have a smaller than a diameter of the disc 702 (or portion of the spiral member) located closer to the trailing edge. For any number of discs 701, 702, the diameter 712 (e.g., 13 mm) of the disc 702 (or portion of the spiral member) at the trailing edge may be the maximum diameter of the layered earplug 700. In many embodiments, the layered earplug 700 may include a tunnel having a 2D face 706, measured at the tip, having a width 708 and a height 710. In some embodiments, the 2D face 706 may be a square with the width 708 being equal to the height 710 (e.g., 1 mm and 1 mm, respectively).

Figure 8:
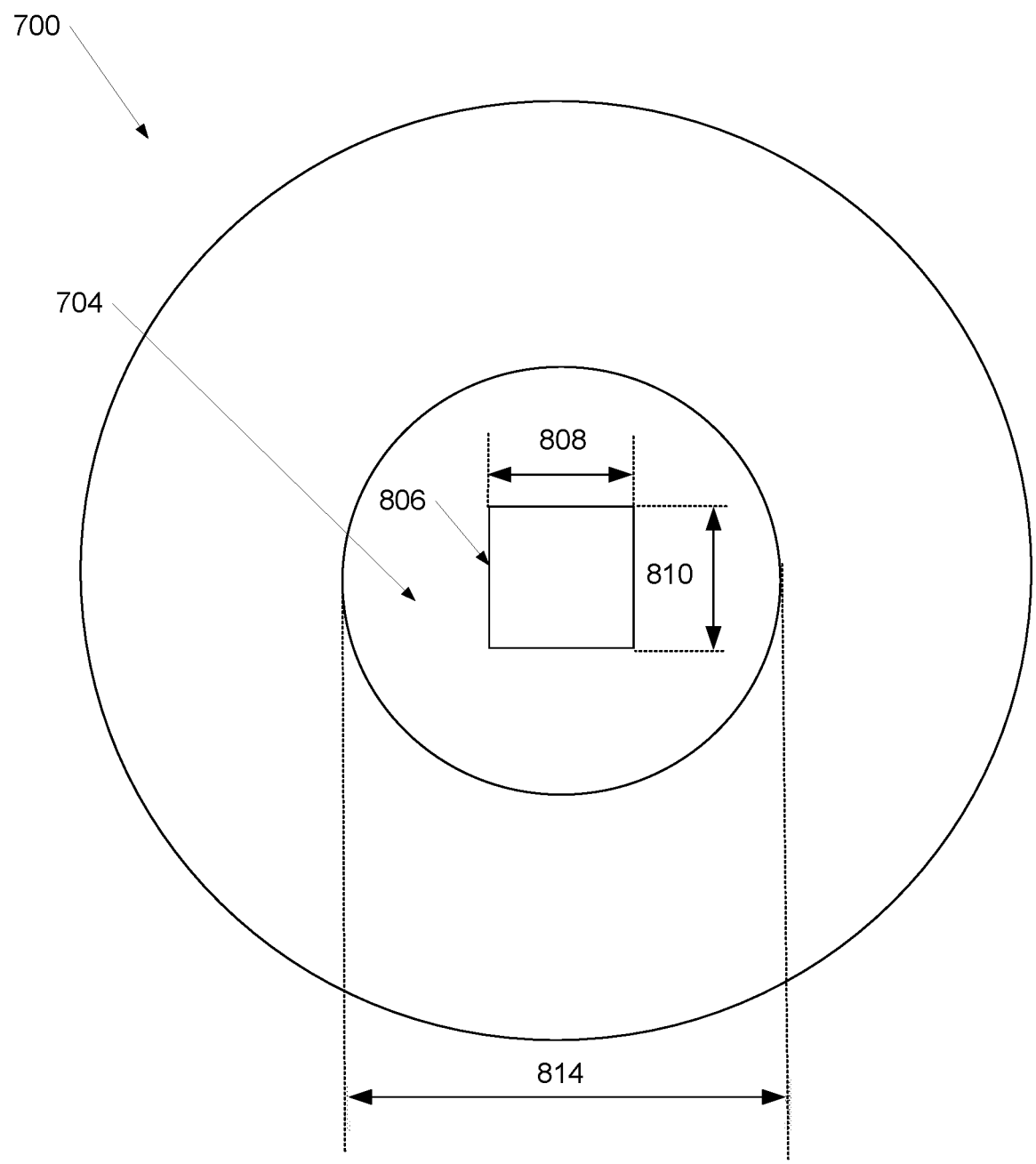
FIG. 8 is a bottom view of a layered earplug with a varying tunnel in accordance with an embodiment of the invention.

A bottom view of a layered earplug with a varying tunnel in accordance with an embodiment of the invention is shown in FIG. 8. With a varying tunnel, the stalk 704 of the layered earplug 700 may include a 2D face 806 having a width 808 (e.g., 2 mm) and a height 810 (e.g., 2 mm). In many embodiments, the tunnel may vary causing a 2D face that is unequal when measured at the tip versus at the end of the layered earplug 700. For example, the 2D face 806 measured at the end of the layered earplug 700 (as illustrated in FIG. 8) may be greater than 2D face 706 measured at the tip of the layered earplug 700 (as illustrated in FIG. 7) (e.g., 2 mm×2 mm versus 1 mm×1 mm). In some embodiments, the 2D face 806 may be a square with the width 808 being equal to the height 810 (e.g., 2 mm and 2 mm, respectively). The stalk may take on various shapes and sized. For example, the stalk 704 may be a cylinder having a diameter 814 (e.g., 5 mm). Although specific layered earplugs with varying tunnels are discussed above with respect to FIGS. 5-8, any of a variety of earplugs including a variety of uniform tunnel shapes, sound reducing and pressure reducing mechanisms as appropriate to the requirements of a specific application can be utilized in accordance with embodiments of the invention. Layered earplugs with varying tunnel shapes in accordance with embodiments of the invention are discussed further below.

While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. A layered earplug, comprising:
   a stalk comprising a tunnel that transverses the layered earplug;
   a plurality of discs attached to the stalk, wherein each disc of the plurality of discs includes a diameter relative to a position of the disc on the stalk;
   at least one air pocket located between two adjacent discs of the plurality of discs, wherein the at least one air pocket and the plurality of discs reduce sound that reaches a user's eardrum; and
   at least one valve located within the tunnel, wherein the at least one valve is configured to release accumulated air pressure in a user's ear canal through the tunnel:
   wherein the at least one valve includes a first end and a second end, wherein the first end is attached to the stalk; and
   wherein the second end of the at least one valve is in contact with the stalk and detached from the stalk allowing the at least one valve to open and release the accumulated air pressure through the tunnel.

2. The layered earplug of claim 1, wherein the tunnel has at least two walls that are opposite and parallel.

3. The layered earplug of claim 2, wherein the stalk includes a tip and an end, and wherein the plurality of discs increases in diameter based on a position moving away from the tip towards the end.

4. The layered earplug of claim 3, wherein the at least one valve is oriented at an angle less than 90 degrees toward the tip and away from the end.

5. The layered earplug of claim 1, wherein the first end of the at least one valve is closer to the tip than the second end of the at least one valve.

6. The layered earplug of claim 1, wherein the plurality of discs is layered with equal space in between each disc of the plurality of discs.

7. The layered earplug of claim 1, wherein the at least one valve is in an open configuration to allow air pressure to escape from within the user's ear canal.

8. The layered earplug of claim 1, wherein the at least one valve is in a closed configuration when air pressure in the user's ear canal has not accumulated above a release pressure.

9. The layered earplug of claim 1, wherein each of the plurality of discs has a thickness of 0.5 mm.

10. The layered earplug of claim 1, wherein each of the plurality of air pockets has a thickness of 0.5 mm.

11. The layered earplug of claim 1, wherein the at least one valve is oriented at an angle of 30 degrees.

12. The layered earplug of claim 1, wherein the at least one valve has a thickness of 0.5 mm.

13. The layered earplug of claim 1, wherein the stalk has a thickness of 5 mm.

14. The layered earplug of claim 1, wherein the stalk has a length of 30 mm.

15. The layered earplug of claim 2, wherein the tunnel is square shaped.

16. The layered earplug of claim 15, wherein the stalk includes a tip and an end, and the tunnel is narrower at the tip than at the end of the stalk.

17. The layered earplug of claim 16, wherein the square shape has sides that are 1 mm at the tip and 2 mm at the end of the stalk.

18. The layered earplug of claim 1 further comprising a handle.

* * * * *